United States Patent
Gomes

[19]

[11] Patent Number: 5,792,077
[45] Date of Patent: Aug. 11, 1998

[54] FEEDBACK GONIOMETER FOR MEASURING FLEXIBILITY OF MEMBER MOVEMENT

[75] Inventor: Francis Gomes, Jersey City, N.J.

[73] Assignee: Bel-Art Products, Inc., Pequannock, N.J.

[21] Appl. No.: 829,408

[22] Filed: Mar. 31, 1997

[51] Int. Cl.$^6$ .................................................. A61B 5/103
[52] U.S. Cl. ............................................................ 600/595
[58] Field of Search ............................ 600/587, 595; 33/511, 512

[56] References Cited

U.S. PATENT DOCUMENTS

| | | | |
|---|---|---|---|
| 4,306,571 | 12/1981 | McLeod, Jr. | 128/782 |
| 4,436,099 | 3/1984 | Raftopoulos | 128/782 |
| 4,804,001 | 2/1989 | McLeod, Jr. | 128/782 |
| 4,834,057 | 5/1989 | McLeod, Jr. | 128/782 |
| 5,263,492 | 11/1993 | Voyce | 128/782 |
| 5,280,265 | 1/1994 | Kramer et al. | 338/210 |
| 5,377,691 | 1/1995 | Boileau et al. | 128/774 |
| 5,435,321 | 7/1995 | McMillen et al. | 128/782 |
| 5,442,729 | 8/1995 | Kramer et al. | 395/2.8 |
| 5,449,002 | 9/1995 | Goldman | 128/779 |
| 5,469,862 | 11/1995 | Kovacevic | 128/782 |
| 5,474,083 | 12/1995 | Church et al. | 128/733 |
| 5,493,788 | 2/1996 | Richardson | 33/512 |

OTHER PUBLICATIONS

Brown et al., The American Journal of Occupational Therapy, Jul. 1979, vol. 33, No. 7, pp. 458–462.

*Primary Examiner*—Max Hindenburg
*Assistant Examiner*—Charles Marmor, II
*Attorney, Agent, or Firm*—Lawrence G. Fridman

[57] ABSTRACT

A goniometer for measuring flexibility and extent of movement of members of a limb connected to a joint consists of first and second arms pivotally connected to each other and a feedback arrangement integrated into the arms. The feedback arrangement includes a generating unit for generating an operational beam, a reflecting unit for reflecting the operational beam, a receiving unit for receiving and analyzing the operational beam reflected from the reflecting unit, an adjustment unit for adjustment of an operational space. The operational space is defined by juxtaposition of the reflecting unit and adjustment unit, whereas an area and angular positioning of the operational space is indicative of the allowable range of movement of members of a limb and the arm elements. An alarm is provided for alarming a user when movement of the arms is not within the allowable range. The alarm is activated when the receiving unit is prevented from receiving the operational beam reflected from the reflecting unit.

12 Claims, 5 Drawing Sheets

FEEDBACK GONIOMETER FOR MEASURING FLEXIBILITY OF MEMBER MOVEMENT

FIELD OF THE INVENTION

This invention relates to devices for medical and therapeutic application and, more particularly, it relates to a goniometer for measurement and monitoring of joint movement.

BACKGROUND OF THE INVENTION

An important, commonly measured physical characteristic of a human body is a range of motion of a particular body joint. The range of motion is the angular movement of one body portion or member of a limb connected to or associated with a joint to that of a second body portion or member of a limb also associated with the same joint. After joint-related illness or injury, it is quite often that a patient is directed to limit the range of motion of a joint and recovery process requires some form of physical therapy. Success of recovery in general, and physical therapy treatment in particular, is typically evaluated by the improved range of motion or flexibility of a treated joint enabling an individual to be ambulatory and functionally independent. Increase of the range of motion of an injured, diseased, burned, paralyzed or post-surgical limb is a primary therapeutic goal of many health care professionals involved in acute treatment and rehabilitation process.

Medical instruments such as goniometers adapted for measuring the range of motion of flexing joints such as knees, ankles, wrists, shoulders, hips, fingers, etc. are known in the art. It is also known for medical instruments or devices to provide feedback signals through receiving video, audio, etc. signals from such instruments reflecting results of exercise, treatment etc. so as to enable patients to relearn, control various physical functions and/or to prevent complications that impede such physical functions. Commonly available medical goniometers are often overly cumbersome, not completely reliable devices which can be difficult to mount and tend to interfere with the motion of a limb they intended to track. Examples of such goniometers are disclosed by the following U.S. Pat. Nos.: 4,306,571; 4,804,001; 4,834,057 all to McLeod, Jr.; 5,263,492 to Voyce; 5,469,862 to Kovacevic; and 5,442,729 to Kramer. As a consequence, such goniometers are not in general use either in acute care, rehabilitation or at home in spite of compelling need.

Thus, it has been a long felt and unsolved need for a medical goniometer capable of accurately measuring the range of motion of a joint and informing a patient when such range of motion is beyond a prescribed limit or when the goal set by the therapist has been reached. Furthermore, there has been a need for a goniometer allowing the clinician to set safe, measurable range of motion goals which are easy to understand and carry out by the patient; a goniometer in which the allowable range of movement can be adjusted prior to operation of the device.

SUMMARY OF THE INVENTION

One aspect of the invention provides a goniometer for measuring flexibility and extent of movement of members of a limb connected to a joint. The goniometer consists of first and second arms pivotally connected to each other and feedback arrangement integrated into these arms. The feedback arrangement includes generating unit adapted for generating an operational beam, reflecting unit for reflecting the operational beam, receiving unit for receiving and analyzing the operational beam reflected from the reflecting unit, adjustment arrangement for adjusting an operational space which is defined by juxtaposition of the reflecting unit and the adjusting unit. The area of the operational space is indicative of the allowable range of movement of the members of the limb and the arm elements. An alarm is provided for alarming user when movement of the arms is not within the allowable range. The alarm is activated when the receiving unit is prevented from receiving the operational beam reflected from the reflecting unit. The adjustment unit is situated between the generating, receiving units and the reflecting unit.

According to another aspect of the invention, the reflecting unit is a reflecting surface and the adjustment unit is an adjustment element movable between the generating, receiving units and the reflecting surface. The adjustment element is formed having a cut-out portion adapted for passage of the operational beam at least from the generating unit to the reflecting surface. The reflecting surface and the adjustment element are rotatably movable relative to each other. The generating unit and the receiving unit are typically situated within the first arm, whereas the reflecting surface and the adjustment element are rotatably connected to the second arm.

As to a further aspect of the invention, when the movement of the first and second arms about a pivotal axis of the goniometer is within a predetermined allowable range, the operational beam is projected through the cut-out portion of the adjustment element into the reflecting surface; and when the pivotal movement of the arms is beyond the predetermined allowable range, a solid part of the adjustment element is interposed between at least the generating unit and the reflecting surface interrupting the operational beam and triggering the alarm. The operational space is adjustable and triggering points of the alarm are set by simultaneous rotation of the second arm with the adjustment element and the reflecting surface about the pivotal axis of the goniometer and rotational motion of the cut-out portion and the reflecting surface relative to each other.

According to still another aspect of the invention, the generating unit is a source of infrared radiation such as light-emitting diode and the receiving means is a radiation beam detector such as transistor, whereby said diode and said transistor are situated within the first arm and the reflecting element is positioned within the second arm.

BRIEF DESCRIPTION OF THE DRAWINGS

Other advantages and features of the invention are described with reference to exemplary embodiments, which are intended to explain and not to limit the invention, and are illustrated in the drawings in which.

3

DESCRIPTION OF THE PREFERRED EMBODIMENT

Figures 1, 2, 18:
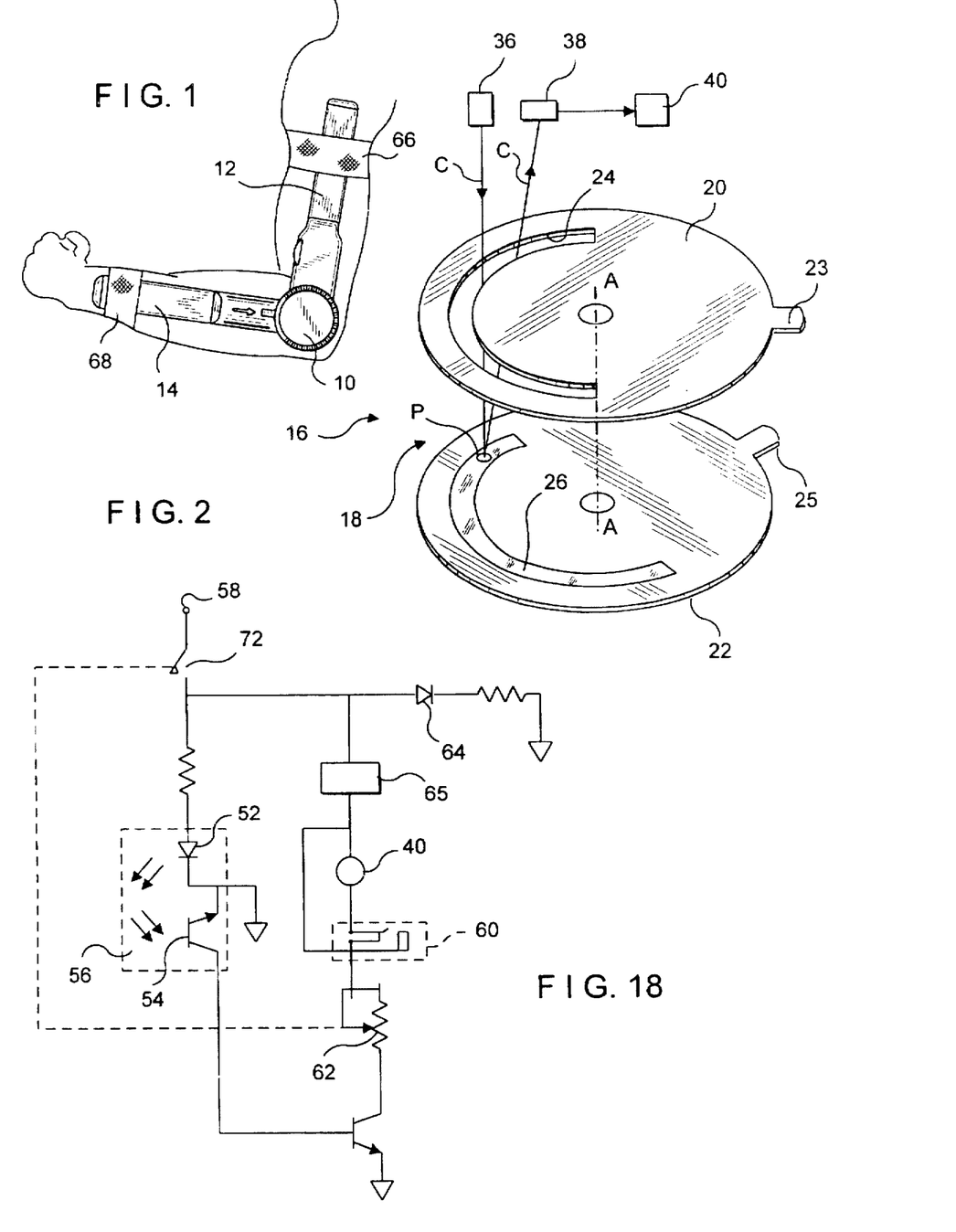
FIG. 1 is a view showing positioning of the goniometer of the invention attached to an elbow for measurement of its flexibility and range of motion.
FIG. 2 is a schematic diagram of a feedback arrangement of the invention.
FIG. 18 is a circuit diagram of the goniometer of the invention.
Figures 3, 4:
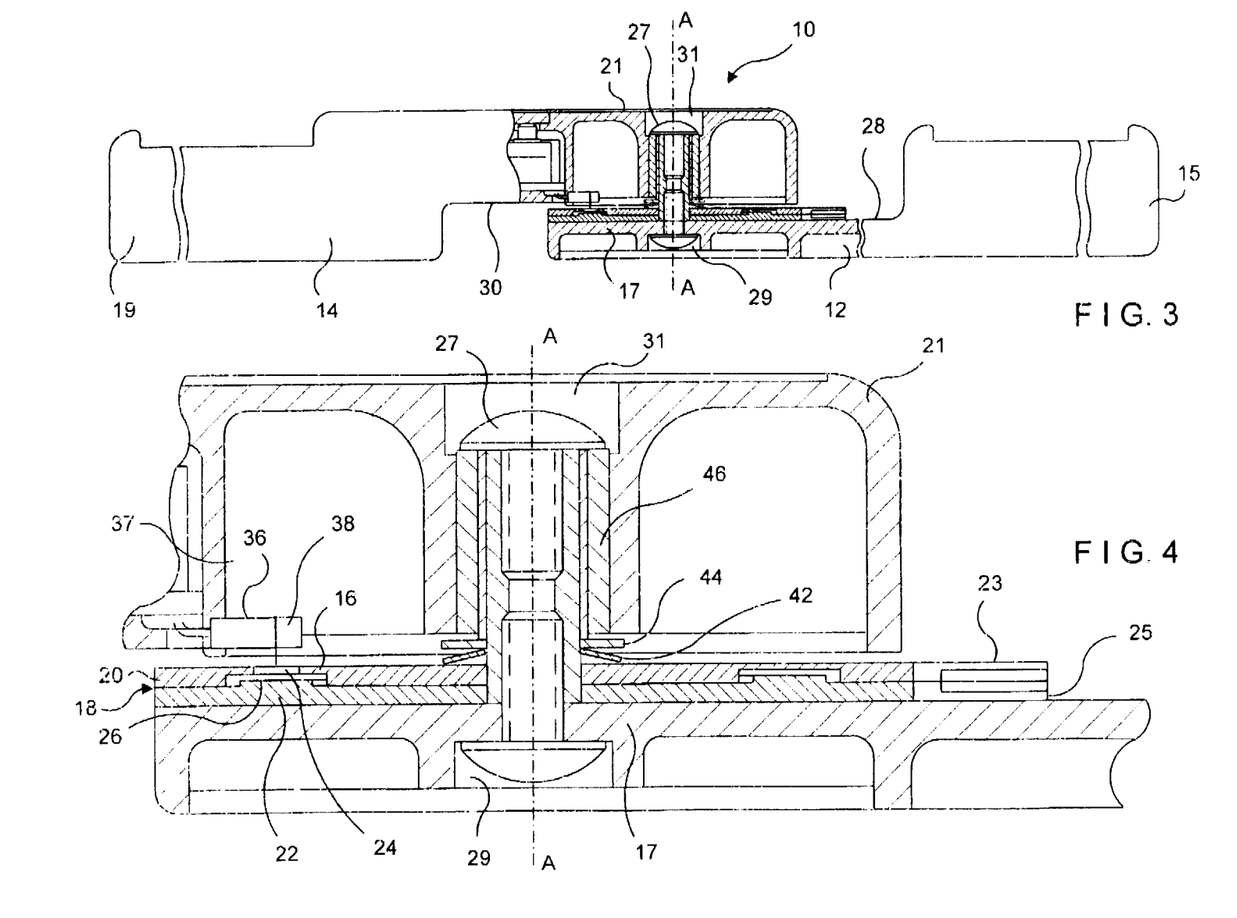
FIG. 3 is a partial cross-sectional view showing the arms of the goniometer.
FIG. 4 is an enlarged, cross-sectional view of the pivotal area.
Figure 5:
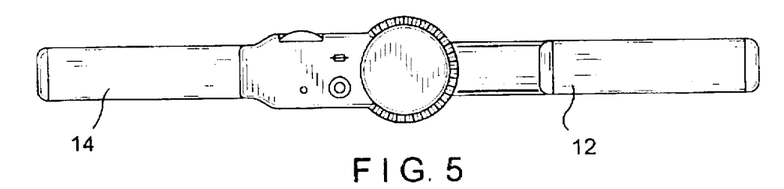
FIG. 5 is a general view of the goniometer of the invention.

Referring now to FIGS. 1–4 wherein a feedback goniometer 10 of the present invention is best shown. It is illustrated in FIGS. 2–4 that a goniometer 10 mainly consists of a first or carrying arm 12 and a second or receiving arm 14 pivotally connected to each other. The carrying arm includes a distal portion 15 adapted for connection to one member of a limb associated with a joint, flexibility of which is measured by the invention, and a proximal portion 17. In a similar manner, the receiving arm 14 contains a distal portion 19 and proximal portion 21. The proximal portions 17 and 21 are formed having connecting apertures 29 and 31 for receiving pivotal members or pins 27 in the assembled condition of the goniometer. To facilitate pivotal movement of the arms relative to one another, the carrying and receiving arms include step-shaped recessed areas 28 and 30 respectively.

A feedback arrangement 16 is integrated into the arms of the invention. In this respect, an internal receiving cavity 37 developed in the proximal portion 17 of the receiving arm is adapted to receive at least a portion of the feedback arrangement. An adjustment element 20 and base element 22 of an adjustment mechanism 18 are connected to and movable with the proximal portion 17 of the carrying arm.

The feedback arrangement 16 typically consists of generating means or a generating unit 36 adapted for generating of an operational beam, reflecting means or a reflector 26 designed to reflect the operational beam and receiving means or a receiving arrangement 38 for receiving and analyzing the operational beam reflected from the reflector 26. An essential function of the adjustment mechanism 18 is to regulate an operational space of the invention during setting operations and use of the goniometer. Alarming means or alarming unit 40 producing audio, video, etc. signals enables the invention to inform a user when angular movement of limb members associated with a joint and corresponding arms of the goniometer are not within the allowable range.

As best illustrated in FIGS. 2–4 and 18, the adjustment mechanism 18 is substantially formed by an adjustment element 20 and a base element 22 rotationally movable about pivotal axis A—A of the goniometer. Although various configurations of these elements are contemplated, in the preferred embodiment of the invention the base and adjustment elements are made as substantially flat diskettes. A cut-out portion 24 passes through the entire thickness of the adjustment element 20. A reflector 26 forms a part of a main surface of the base element 22 facing the adjustment element in the assembled condition of the invention. In the preferred embodiment, the cut-out portion 24 and reflector 26 are formed as semicircular or arc-shaped segments at least partially extending along the periphery of the corresponding diskettes. Nevertheless, any suitable configuration and angular extension of the cut-out portion and the reflector are within the scope of the invention. To facilitate operation of the adjustment mechanism 18, the diskettes are provided with tabs 23 and 25 extending outwardly from respective outside peripheries thereof.

The operational space of the invention is defined by juxtaposition of the cut-out portion 24 and the reflector 26 and is typically represented by a portion of the reflector 26 unobstructed by a solid part of the adjustment element 20. The area of the operational space varies upon degree of juxtaposition of the cut-out portion 24 and the reflector 26. As discussed hereinbelow, the area and angular positioning of the operational space relative to the feedback arrangement in general and specifically relative to the operational beam substantially defines the allowable range of angular movement of the arms of goniometer and monitored body joint.

In the assembled condition of the invention (see FIGS. 3 and 4), the adjustment and base elements are situated within a space between the carrying and receiving arms. The base element 22 is arranged at an interior surface of the proximal portion 17 of the carrying arm in such a manner that the reflector 26 faces the adjustment element 20 as well as the generating unit 36 and the receiving unit 38 situated within the internal cavity 37 of the receiving arm 14.

In the adjustment mechanism assembly 18 the frictional forces between the base element 22, adjustment element 20 and the proximal portion 17 of the carrying arm are greater than the frictional forces between these elements and the proximal portion 21 of the receiving arm. Enhanced engagement between the elements 20 and 22 of the adjustment mechanism and the carrying arm 12 is a result of a pressure exerted by a spring 42 forcing the diskettes into engagement with each other and the proximal portion 17. As illustrated in FIGS. 3 and 4, the spring 42 is interposed between a washer 44 of a bearing unit 46 and a surface of the adjustment element 20 remote from the base element 22. Each element of the adjustment mechanism is independently rotatable through the respective tabs 23 and 25 relative to each other and about pivotal axis A—A of the goniometer and carrying arm 12. In operation of the goniometer 10, the adjustment and base elements together are rotatable with and carried by the carrying arm 12.

The base element of the adjustment mechanism can be situated in an enclosed area formed within the proximal portion of the carrying arm (not shown). Such enclosed area further protects the adjusting mechanism assembly 18 and the base element 22 from outside light. To minimize possibility of the operational beam losing its intensity while traveling to and from the reflector 26, the distance between the outer end of the receiving cavity 37 (which accommodates the generating unit 36 and the receiving arrangement 38) and the reflector 26 should be as small as possible. In this respect, if the distance between the sensor and the reflector is substantially greater than 1/16", the resolution of the apparatus of the invention might decrease. Thus, in one embodiment of the invention, each diskette can be made having the thickness of about 1/32" and the reflector 26 mounted on the upper surface of the base element is situated at a short distance from the generating arrangement and the sensor.

In order to restrict passage of the operational beam only through the cut-out portion 24 and to prevent penetration of the radiation to and from the reflector through any other parts of the adjustment element 20, it is typically made of solid, impermeable to light radiation material.

To further reduce undesirable interference of the outside light radiation with operation of the invention, both arms including the internal cavity 37 of the receiving arm are also made from a material impermeable to an outside light radiation as well as to the operational beam of the goniometer.

As indicated hereinabove, the operational space of the invention is defined by juxtaposition of the reflector 26 and the cut-out portion 24. An area of the operational space, its angular positioning relative to the operational beam are indicative of the allowable range of movement of the limb members associated with the joint. The operational angle is the angle of movement of the arms of the goniometer including the operational space relative to the operational beam and its projection on the reflector 26. The operational angle can be also defined as the angle of movement of the operational space and the projection of the operational beam relative to each other.

The adjustment of the area of the operational space occurs upon rotational movement of the cut-out portion 24 of the adjustment element relative to the reflector 26 of the base element. In the preferred embodiment of the invention, the angular extension of the operational space varies between 0° and 180°. In 180° position, the cut-out portion is fully juxtaposed over the reflector, so that the entire area of the reflector is open and available for interaction with the operational beam. In the 0° condition, the entire area of the reflector is closed by the solid part of the adjustment element.

Upon adjustment of the operational space to a predetermined value, the base and adjustment elements are kept together by the frictional forces exerted on the adjustment mechanism by the spring 42. Therefore, the operational space formed by the juxtaposition of the base and adjustment elements travels with the carrying arm 12 relative to the operational beam in general and specifically, relative to the projection of the operational beam on the reflector 26.

When the angular motion of the arms of the goniometer 10 is within the predetermined range of the operational angle of the device defined in the initial setting procedure, the operational beam C after its passage through the cut-out portion 24 is received by the reflector 26 and reflected back through the cut-out portion 24 in the direction of the receiving arrangement or sensor 38 (see FIG. 2). However, upon shifting of the arms of the goniometer to a position beyond the allowable range of operational angle, the operational space, formed by the base and adjustment elements carried by the carrying arm 12, is also shifted. In this condition, a solid portion of the adjustment element 20 is interposed between the operational beam and the reflector interrupting the flow of operational beam. As discussed hereinbelow, such interruption through the electronic circuitry of the invention activates an alarm unit.

The electronic circuitry of the goniometer of the invention is best illustrated in FIG. 18. As illustrated in FIG. 18 as well as in FIGS. 1 and 2, the operational beam is generated by the generating unit 36 which in the preferred embodiment of the invention can be a photo-diode 52 capable of generating and emitting an infrared radiational beam. In the preferred embodiment, the receiving arrangement 38 adapted for receiving and analyzing the operational beam reflected from the reflector 26 is a sensor-detector such as a photo-transistor 54. The generating unit and the sensor-detector can be formed as independent components or can be combined in OPTO-SENSOR unit 56 situated in the receiving cavity 37 of the receiving arm 14. In the preferred embodiment, an infrared beam generated by the photo-diode 52 is directed towards the adjustment mechanism 18 associated with the proximal portion of the carrying arm 12. It is known that a transistor is an electronic device utilizing a small change in current to produce a large change in voltage, current or power. In the present invention, the transistor functions as an electronic switch which, in response to receiving the reflected infrared beam, turns on or off a larger current flow from the power unit 58 to the alarm 40.

In operation, an uninterrupted operational infrared beam is directed from the diode 52 to the reflector 26 and from the reflector to the photo-transistor 54. This occurs when a user operates the goniometer within the predetermined range of operational angle or motion of a joint, properly defined during the initial setting. In this condition, a part of the reflector 26 adapted for receiving of the projection of the operational beam has not been blocked by a solid portion of the adjustment element 20. The photo-transistor 38 operates in the cut-off mode, the circuit is open and no current is flowing from the power unit to the alarm 40. As a result, no audio, video, etc. signals are generated.

However, when the angular motion of the limb members and corresponding arms of the invention extend into the operational sector situated beyond the allowable limits of operational angle established in the setting procedure, position of the operational space is shifted, so that the operational beam is interrupted. This occurs when the reflector 26 is blocked and the operational beam is projected on the solid portion of the adjustment element on either side of the operational space.

In this condition, since the sensor-detector or transistor 54 stops receiving the reflected operational beam, a signal is generated switching the transistor to a saturation mode. In the saturation mode, the transistor 54 allows the current to flow at the maximum rate in one direction, that is from the power unit 58 to the alarm 40, energizing the latter and generating an appropriate audio, video, etc. signal. Thus, the user is informed that members of a limb connected to a joint and the corresponding arms of the goniometer move beyond the allowed limits of motion.

As to other components, the circuitry has been provided with volume control 62 and power on-off indicator 64. The volume control 62 basically controls the intensity of the current flow through the alarm unit. The on-off switch 72 enables the user to turn off the power when the invention is not in use. An external signal output 60 and an alarm signal driver 65 are also provided.

Although the operational beam of infrared spectrum has been utilized in the preferred embodiment of the invention, any type of optical radiation capable of being reflected from the reflector and accepted by the receiving arrangement is within the scope of the invention. The infrared operational beam has been chosen in view of the distinctions between the infrared radiation and an outside, ambient light. Therefore, the outside light cannot trigger the alarming unit of the goniometer, reducing chance of false alarms and making the invention more precise and less susceptible to an outside interference.

There are three relative situations reflecting movement of the elements of the adjustment assembly 18 during operation of the device. In the first situation, the adjustment 20 and base 22 elements are movable relative to each other and about pivotal axis A—A of the goniometer. In the second situation, the base element 22 carrying the reflector 26 is movable, whereas the adjustment element 20 having the cut-out portion 24 is stationary. In the third situation, the base element is stationary and the adjustment element having the cut-out portion is movable about the base.

In operation, the pivotal connection is proximally positioned in the direct vicinity of the joint, the range of motion and flexibility of which is measured by the goniometer of the invention. The operational angle at which the arms of the goniometer move relative to each other, while positioned at the limb members, constitutes direct measurement of flexibility and/or range of motion of the joint.

With affixation of the arms of the goniometer to limb members, continuous, real live readings can be taken associated with the joint. Alternatively, the goniometer can be merely placed against a joint such as knee, elbow, wrist, etc. for a single instantaneous measurement.

The goniometer of the invention can be placed on either lateral side of a joint for appropriate monitoring and measurement. At least two straps 66 and 68 (see FIG. 1) are provided for connecting the arms of the goniometer to the limb members on either side of the joint. The straps are adapted for holding the feedback goniometer in place on the joint. With such straps, the goniometer can be readily worn for continuous monitoring and measurement of the movement of the limb members during actual use. The straps can be formed with any conventional fastening means or arrangement permitting rapid deployment and removal as well as providing a large holding range for use with patients having limbs of different dimensions. One of such fastening arrangements could be hook and eye fasteners, also known as VELCRO.

Setting of the predetermined ranges of the operational angle as well as operation of the feedback goniometer of the present invention is best illustrated in FIGS. 6–18. Although three operational and setting modes of the invention are illustrated in these Figures, other modes are within the scope of the invention. In the foregoing discussion, for the sake of convenience, the carrying arm 12 carrying the base and adjustment elements is indicated as being movable, while the receiving arm 14 supporting the generating unit and receiving arrangement is stationary. It should be realized, however, that operational modes of the invention having the carrying arm in the stationary condition and movable receiving arm as well as both arms movable are also contemplated. The operation of the goniometer of the invention in general, and adjustment, setting procedures in particular, are being described with reference to clockwise and/or counter-clockwise rotational movement of the carrying arm. Such clockwise and/or counter-clockwise motion also represents the directions of the angular movement of the limb members associated with the joint which measured range of motion should be, at least partially, limited by the user. For example, in the counter-clockwise rotational mode, the alarm unit is activated and the user is informed when the carrying arm and corresponding limb member, while moving in the counter-clockwise direction, reach the preset range of operational angle. Similarly, in the clockwise operational mode, the alarm unit is activated when the carrying arm and corresponding limb member, when moving in the clockwise direction, reach the preset range of operational angle.

Figures 6, 7, 8, 9, 10:
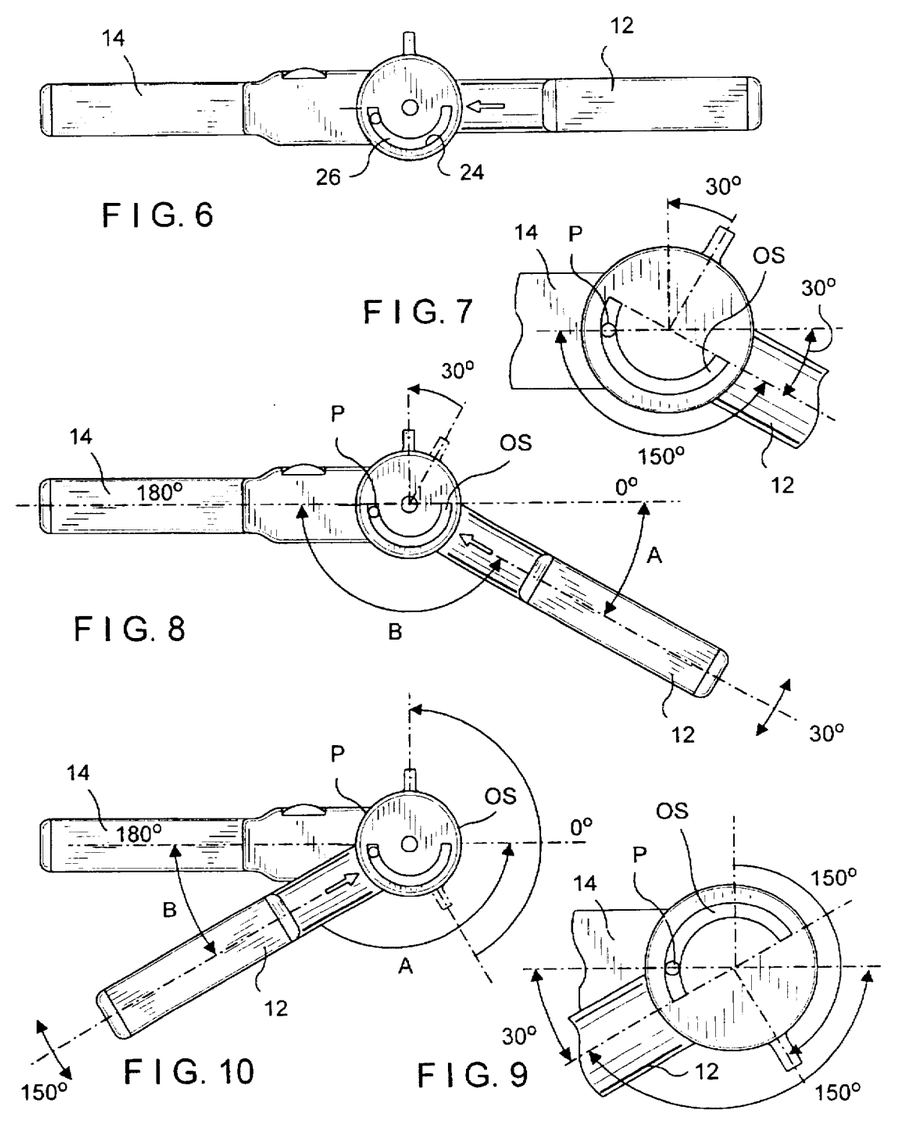
FIG. 6 shows an initial position of the arms in the counter-clockwise rotational adjustment setting mode.
FIG. 7 illustrates an intermediate positioning of the arms and operational opening for a first embodiment of the counter-clockwise rotational setting mode.
FIG. 8 illustrates final positioning of the arms and operational opening in the first embodiment of the counter-clockwise rotational setting mode.
FIG. 9 shows an intermediate positioning of the arms and operational opening for a second embodiment of the counter-clockwise rotational adjustment setting modes of the invention.
FIG. 10 illustrates final positioning of the arms and operational opening in the second embodiment of the counter-clockwise rotational adjustment setting mode.

We are now referring to FIGS. 6–10, wherein the counter-clockwise rotational adjustment mode of the invention is best illustrated. Initially, an example will be discussed in which a single trigger point of the alarm is set for 30° position in the counter-clockwise rotational motion of the carrying arm. In this example, in the counter-clockwise rotational motion of the carrying arm and corresponding limb member, the allowable operational angle or rotational sector B is being set between about 180° and 30° and the alarm is activated upon the carrying arm reaching and/or moving below 30° position. The undesirable operational sector A is being set between 30° and 0° of the rotational motion of the carrying arm and corresponding limb member. Initially, the device is adjusted, so that the arms are situated substantially at 180° position to each other (see FIG. 6). The carrying arm 12 with base and adjustment elements is then rotated clockwise 30°, so that the angle between the axis of the receiving arm 14 and the axis of the carrying arm 12 is 150° (see FIG. 7). In this condition, the operational space OS is also shifted 30° clockwise relative to its initial position shown in FIG. 6. Then, as illustrated in FIG. 8, the base and adjustment elements only, through their respective tabs, are simultaneously rotated 30° counter-clockwise about the pivotal axis of the goniometer and carrying arm (the latter at the moment is kept stationary), to the initial position of the operational space shown in FIG. 6. It is important to understand that in this operational mode, after the setting adjustments are accomplished as discussed hereinabove, the carrying arm 12 as well as the base and adjustment elements forming the operational space OS are moved together relative to a substantially stationary receiving arm 14, generating unit or diode 36 and the projection P of the operational beam. Thus, in the final position of this mode (see FIG. 8) the carrying arm and the corresponding limb member associated with the joint are movable within the allowable preset operational sector B (between 30° and 180° ). In this condition, the operational beam through the operational space is projected into (see the projection P) and reflected from the reflector 26 and accepted by the sensor. However, when the carrying arm in its counter-clockwise rotational motion, or otherwise, moves within the operational sector A (between 30° and 0°), the base and adjustment elements defining the operational space are also moved counterclockwise relative to a substantially stationary projection P of the operational beam, so that the projection P is situated outside the operational space OS and the reflector. In this condition (not shown), the operational beam is interrupted by a solid part of the adjustment element triggering the alarm.

FIG. 10 illustrates an example of setting the goniometer of the invention for a single alarm trigger point in the counter-clockwise rotational mode of the carrying arm when it is movable without triggering the alarm within the allowable operational sector B (between 150° and 180°). The undesirable operational sector A is between 0° and 150°. FIG. 9 illustrates an intermediate step similar to that of FIG. 7. In this embodiment, the steps of operation of the invention are similar to that of FIGS. 6–8.

Figure 11:
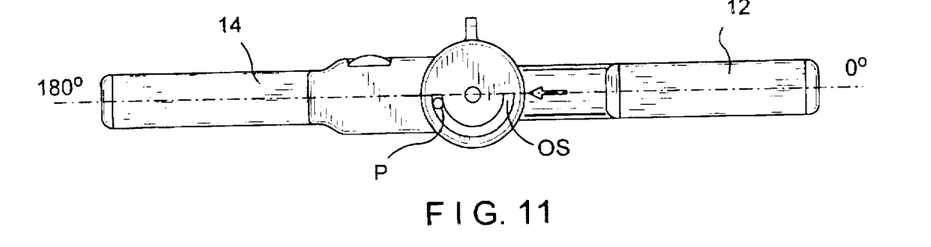
FIG. 11 illustrates initial positioning of the arms and operational opening in the clockwise rotational adjustment setting mode.
Figure 12:
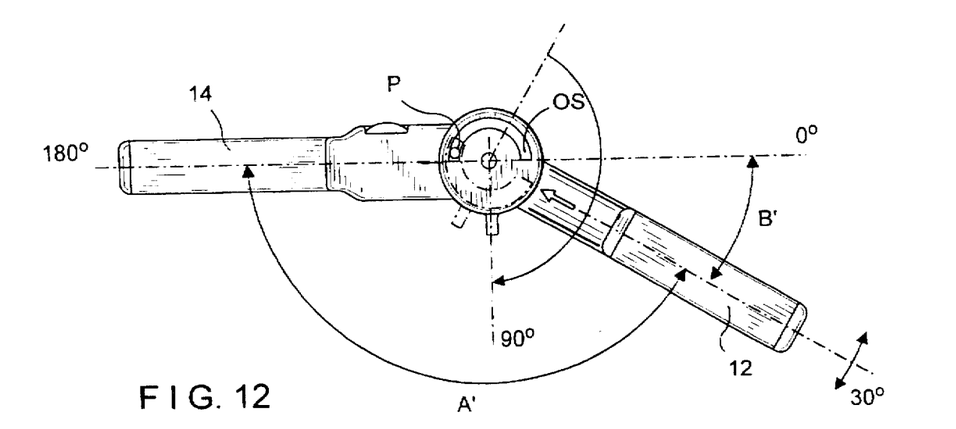
FIG. 12 illustrates positioning of the arms and operational opening for the first embodiment of the clockwise rotational setting mode.
Figures 13, 14:
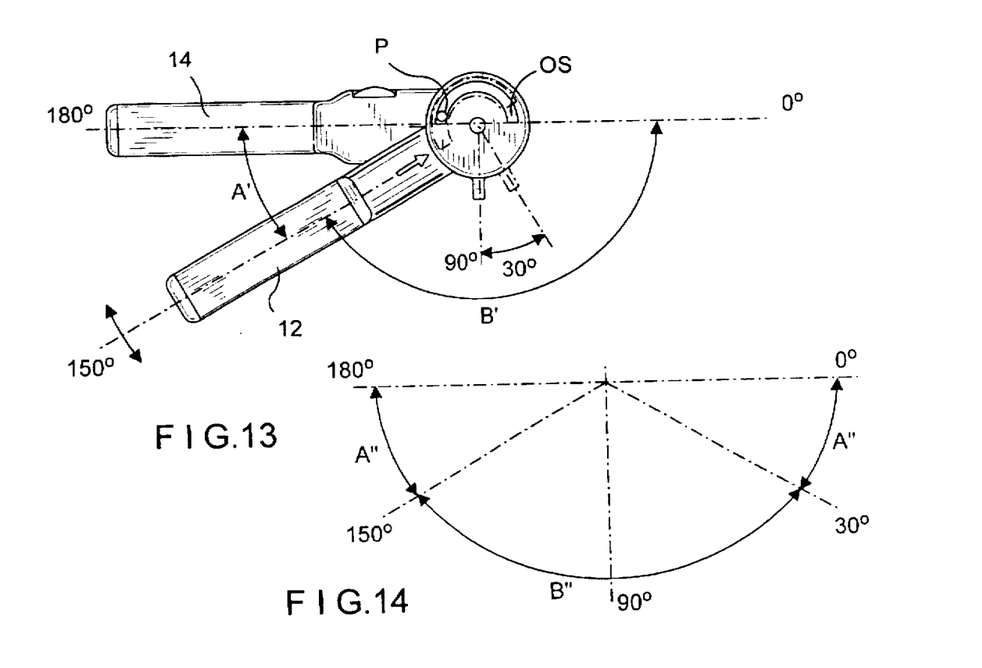
FIG. 13 illustrates positioning of the arms and operational opening for a second embodiment of the clockwise rotational setting mode.
FIG. 14 is a diagram illustrating a setting mode with double trigger point alarm setting.

The clockwise operational setting modes of the invention are best illustrated in FIGS. 11–13. Similar to the above-discussed embodiments, initially, prior to setting of a single trigger point, both arms are positioned at 180° angle to each other (see FIG. 11). As illustrated in the example of FIG. 12, to arrange a single trigger point setting, the carrying arm, along with base and adjustment elements, is rotated 30° clockwise. In this intermediate position the operational space OS is also shifted 30° clockwise as illustrated in dotted lines on FIG. 12. This position of the carrying arm is similar to the position illustrated in FIG. 7. Then, both elements of the adjustment mechanism together through their respective tabs are rotated with respect to the pivotal axis of the goniometer to a position in which the operational space OS is placed in the position illustrated by solid lines in FIG. 12. Thus, the carrying arm and a corresponding limb member are allowed to move, without triggering the alarm, within the operational sector B' (between 0° and 30°). The undesirable area of motion of the carrying arm and the corresponding member of a limb in this setting arrangement is situated within the operational sector A' (between 30° and 180°). Thus, the alarm is activated upon reaching and/or exceeding 30° position by the carrying arm. After the setting steps and during operation of the invention the carrying arm 12 and the elements forming the operational space OS are kept together, while the carrying arm and the operational space are allowed to move. When this occurs without triggering the alarm i.e. within the operational sector B' (between 0° and 30°), the projection of operational beam P is situated on the reflector 26. However, upon carrying arm moving clockwise beyond 30° position range (i.e. the carrying arm moves and operates within the operational sector A' between 30° and 180°), the operational space OS is shifted away from the substantially stationary projection P of the operational beam. Thus, a solid part of the adjustment element is, interposed between the operational beam and the reflector, interrupting the operational beam and triggering the alarm.

FIG. 13 illustrates the setting procedure for an embodiment of the invention with a single trigger point of the alarm unit when the carrying arm and the corresponding limb member are allowed to move within the operational sector B' (between 0° and 150°). The corresponding undesirable zone of movement A' is within the operational sector between 150° and 180°. In this setting, the carrying arm and the elements defining the operational space are initially rotated clockwise from 0° to 150° position. This position of the operational space is illustrated by dotted lines in FIG. 13. Then, both base and adjustment elements defining the operational space are rotated about the pivotal axis of the device and the stationary carrying arm 12 to a position shown by solid lines in FIG. 13. Thus, the unit is set for the alarm to be activated when the carrying arm is rotated clockwise beyond 150° position and within the operational sector A' (between 150° and 180°).

Figure 15:
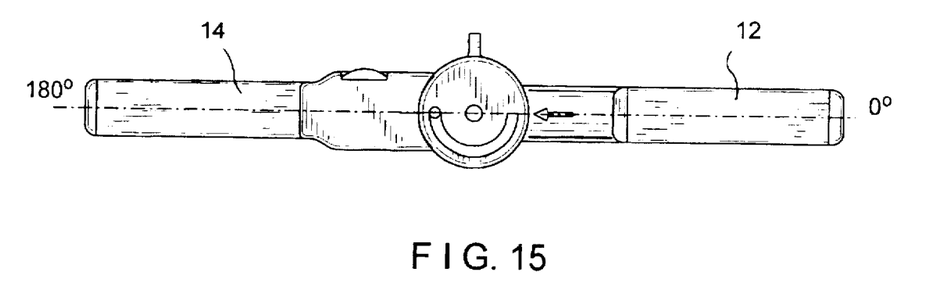
FIG. 15 shows initial positioning of the arms and operational opening for the double trigger point alarm setting.
Figure 16:
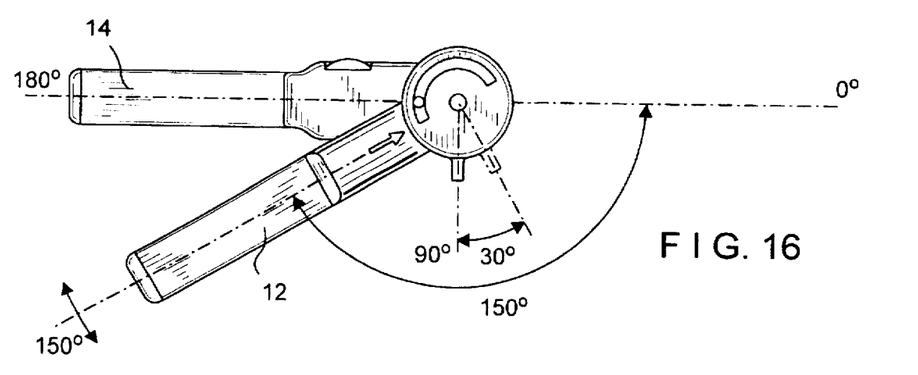
FIG. 16 illustrates one setting position of the arms and operational opening for the double trigger point alarm setting.
Figure 17:
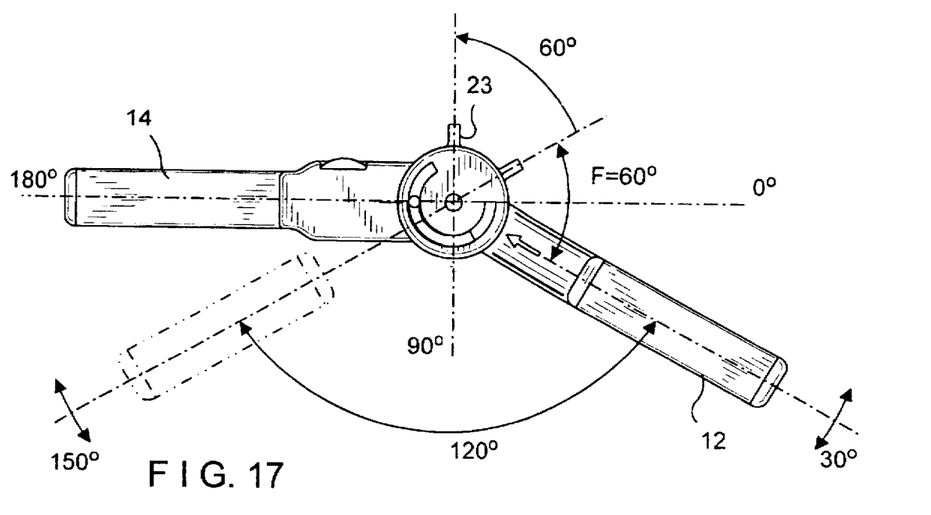
FIG. 17 illustrates another setting position of the arms and operational opening for the double trigger point alarm setting.

The third operational mode of the invention is best illustrated in FIGS. 14–18. As shown in FIG. 14, the undesirable range of rotational movement of the carrying arm is defined by two operational sectors A" (between 0° and 30° and between 150° and 180°). The allowable area of movement of the carrying arm and the corresponding limb member, without triggering the alarm, is within the operational sector B" (between 30°–150°). This operational mode requires double trigger point alarm setting: when the rotational arm movement goes either below 30° or above 150° area. The initial positioning of the elements of the invention illustrated in FIG. 15 is similar to that shown in FIGS. 6 and 11. The carrying arm and the element defining the operational space are then rotated 150° clockwise. After that, the elements defining the operational space OS through the respective tabs are rotated together 30° clockwise about the stationary carrying arm to the position illustrated in solid lines in FIG. 16. At this point, the positioning of the operational space is similar to that illustrated in FIG. 13. This accomplishes setting of 150° trigger point. In order to set the 30° trigger point, the carrying arm is rotated counter-clockwise to the position illustrated in solid lines in FIG. 17 so that the angle F between the longitudinal axis of the carrying arm and that of the tabs is about 60°. From this position, the adjustment element 20 only through its own tab 21 is rotated with respect to the carrying arm 12 and the base element 22. Thus, the cut-out portion of the adjustment element is shifted 30° with respect to the reflector of the base element. Therefore, the operational space is now defined by the cut-out portion and the reflector juxtaposed over each other and is just 120°. In view of the above, in this condition, the device of the invention is set for the alarm unit to be activated when the carrying arm moves within the operational sectors A" (between 0° to 30° and 180°–150°).

The apparatus of the invention is intended for use by means of incentive or disincentive goniometer. In the case of incentive goniometer, the apparatus of the invention can be applied, for example, to a knee which is substantially stiff from having undergone a total knee replacement. The apparatus of the invention is typically set to an angle of knee flexion (i.e. 45°) which is set as a therapeutic goal for user to achieve. The user attempts to actively flex his knee and is aware of reaching a goal when the alarming unit is triggered. In a subsequent treatment, the degree of knee flexion could be advanced to a further range (i.e. to 55°) to encourage the user to achieve increased knee flexion.

Conversely, when the apparatus is used as disincentive goniometer, it would act as a warning device. In this mode, if a user is restricted from flexing to more than 90° while exercising the knee, the alarming unit of the device of the invention alerts the user to stop the exercise or knee flexion when 90° of knee flexion is reached.

What is claimed is:

1. A goniometer for measuring flexibility and extent of movement of members of a limb connected to a joint, said goniometer comprising:

first and second arms pivotally connected to each other;
a feedback arrangement integrated into said arms, said feedback arrangement including generating means for generating an operational beam, reflecting means having a surface for reflecting said operational beam receiving means for receiving and analyzing said operational beam reflected from said reflector means, adjustment means for adjustment of an operational space, said operational space is defined by juxtaposition of said reflecting means and adjusting means, an area and angular positioning of said operational space being indicative of allowable range of movement of members of a limb and said arm elements, alarming means for alarming a user when movement of said arms is not within the allowable range, said alarming means being activated when said receiving means is prevented from receiving said operational beam reflected from said reflecting means.

2. The goniometer of claim 1, wherein said adjustment means is positioned between said generating means, receiving means and said reflecting means.

3. The goniometer of claim 2, wherein said reflecting means is a reflector and said adjustment means is an adjustment element movable between said generating, receiving means and said reflecting surface, said adjustment element having a cut-out portion adapted for passage of the operational beam at least from said generating means to the reflector, said reflector and said adjustment elements are pivotably movable relative to each other.

4. The goniometer of claim 3, wherein said generating means and said receiving means are situated within said first arm, whereas said reflector and said adjustment element are pivotable about a pivotal axis of the goniometer and carried by said second arm.

5. The goniometer of claim 4, wherein when said movement of said arms about the pivotal axis of the goniometer is within a predetermined allowable range said operational beam is projected through the cut-out portion of the adjustment element on said reflecting surface; and when said movement of said arms is beyond said predetermined allowable range a solid part of the adjustment element is interposed between at least said generating means and said reflector interrupting said operational beam and triggering said alarm means.

6. The goniometer of claim 5, wherein said operational space is adjusted and triggering points of said alarm unit are set by rotation of the second arm carrying the adjustment element and the reflecting surface about the pivotal axis of the goniometer and pivotal motion of said cut-out portion and said reflecting surface relative to each other.

7. The goniometer of claim 5, wherein said generating means is a source of an infrared radiation comprising a light emitting diode and said receiving means is a radiation beam detector comprising a photo-transistor, whereby at least said diode is situated within said first arm and said reflector is carried by said second arm.

8. The goniometer of claim 7, wherein said phototransistor is situated within said first arm.

9. A goniometer for measuring extent of angular movement of a limb about a joint, said goniometer comprising:

first and second arms pivotally connected to each other, said arms being positioned coextensively with members of a limb connected by a joint;

a feedback arrangement integrated into said arms, said feedback arrangement including generating means for generating an operational beam, reflecting means having a surface for reflecting said operational beam, receiving means for receiving and analyzing said operational beam reflected from said reflector means, adjustment means for adjustment of an operational space, said operational space is defined by juxtaposition of said reflecting means and adjustment means, an area of said operational space being indicative of allowable range of movement of said members of a limb and said arm elements, alarming means for alarming a user when movement of said members of a limb and said arms is not within the allowable range, said alarming means being activated when said receiving means is prevented from receiving said operational beam reflected from said reflecting means.

10. The goniometer of claim 9, wherein said reflecting means is a reflector and said adjustment means is an adjustment element movable between said generating, receiving means and said reflecting surface; said adjustment element having a cut-out portion adapted for passage of the operational beam at least from said generating means to the reflector, said reflector and said adjustment elements are rotatably movable relative to each other.

11. The goniometer of claim 10, wherein said generating means and said receiving means are situated within said first arm, whereas said reflector and said adjustment element are pivotable about a pivotal axis of the goniometer and carried by said second arm.

12. The goniometer of claim 11, wherein when said movement of said arms about a pivotal axis of the goniometer is within a predetermined allowable range said operational beam is projected through the cut-out portion of the adjustment element into said reflecting surface and when said movement of said arms is beyond said predetermined allowable range, a solid part of the adjustment element is interposed between at least said generating means and said reflecting surface interrupting said operational beam and triggering said alarm means.

* * * * *